United States Patent [19]

Dehner et al.

[11] Patent Number: 5,722,408
[45] Date of Patent: Mar. 3, 1998

[54] METHOD FOR IMAGE GENERATION IN AN IMAGING SYSTEM OF MEDICAL TECHNOLOGY

[75] Inventors: Guenter Dehner, Erlangen; Manfred Herbert, Erlange-Buechenbach, both of Germany

[73] Assignee: Siemens Aktiengesellschaft, Munich, Germany

[21] Appl. No.: 742,214

[22] Filed: Oct. 31, 1996

[30] Foreign Application Priority Data

Nov. 7, 1995 [DE] Germany ............ 195 41 500.0

[51] Int. Cl.⁶ .................................................. A61B 6/00
[52] U.S. Cl. ................ 128/653.1; 378/4; 378/901; 395/118; 395/924
[58] Field of Search ............... 128/653.1, 653.2; 378/4, 901; 395/118, 141, 924

[56] References Cited

U.S. PATENT DOCUMENTS 4,984,157  1/1991  Cline et al. ................ 395/124

Primary Examiner—Ruth S. Smith
Attorney, Agent, or Firm—Hill, Steadman & Simpson

[57] ABSTRACT

In a method for image generation in an imaging system which permits an additional sectional image with arbitrary orientation to be efficiently and quickly calculated during the generation of the individual tomograms or sub-volume images, an image data set that represents a two-dimensional sectional image having an arbitrary orientation relative to the parallel slices or sub-volumes is acquired from the three-dimensional volume data set of the image data during the reconstruction of individual tomograms or sub-volume images. A three-dimensional evaluation thus already becomes possible during the measurement and reconstruction.

9 Claims, 2 Drawing Sheets

METHOD FOR IMAGE GENERATION IN AN IMAGING SYSTEM OF MEDICAL TECHNOLOGY

BACKGROUND OF THE INVENTION

1. Field of the Invention

The present invention is directed to a method for generating an image in a medical imaging system, and in particular to such a method wherein a two dimensional tomogram with an arbitrary orientation is calculated from a three-dimensional volume data set.

2. Description of the Prior Art

It is known in medical technology to generate image data (volume data) that embody a volume image. For example, such image data can be generated with a computed tomography apparatus by conducting a spiral scan of the subject. U.S. Pat. No. 4,984,157 discloses a method wherein a two-dimensional, planar tomogram is selected, calculated and displayed from an already existing image volume data set that is stored in a memory. A completely existing image volume data set is required for this purpose.

In a technique known as multiplanar reformatting (MPR) in a computed tomography apparatus, calculation of a two-dimensional tomogram with an arbitrary orientation is undertaken from a three-dimensional volume data set that describes a volume image. This three-dimensional volume data set is acquired, for example in computed tomography, by calculating a sequence of two-dimensional tomograms that lie in the x-y plane at predetermined z-coordinates.

SUMMARY OF THE INVENTION

An object of the present invention is to provide a method of the type initially described wherein an image in a two-dimensional sectional plane with arbitrary orientation is efficiently and quickly calculated from a three-dimensional volume data set.

In the inventive method, the desired, additional two-dimensional tomogram (MPR image) with arbitrary orientation is calculated simultaneously together with the measurement and reconstruction of the original tomograms or images of a sub-volume. This MPR image is then displayed simultaneously with the presentation of the original tomograms or sub-volume images on screen of a monitor. The MPR image grows during the course of the reconstruction (growing MPR). A three-dimensional evaluation is thus already possible during the measurement and reconstruction.

DESCRIPTION OF THE PREFERRED EMBODIMENTS

Figure 1:
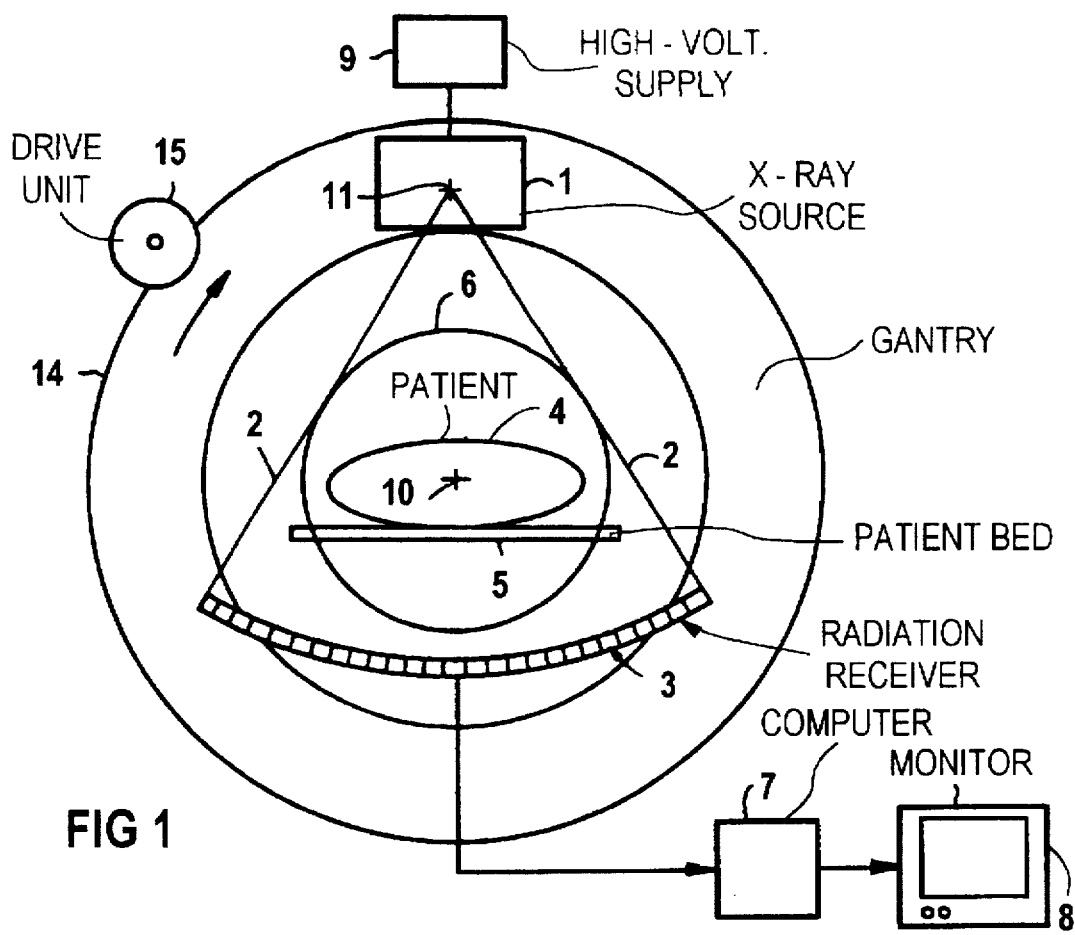
FIG. 1 is a block diagram computed tomography apparatus for explaining the inventive method.

The computed tomography apparatus shown in FIG. 1 has a measuring unit composed of an x-ray source 1 that emits a fan-shaped x-ray beam 2, and a radiation receiver 3 which is composed of a series of individual detectors, for example 512 individual detectors. The focus is referenced 11. The patient 4 to be examined lies on a patient bed 5. The x-ray source 1 and the radiation receiver 3 are mounted on a gantry 14, surrounding the patient 4. For scanning the patient 4, the measuring unit composed of the x-ray source 1 and the radiation receiver 3 is rotated by 360° around a measuring field 6 in which the patient 4 lies. This is accomplished by rotating the gantry 14 round a rotational axis 10 by means of a drive unit 15. The x-ray source 1 that is supplied by a high voltage generator 9 can be pulsed or operated to emit continuous radiation. Sets of data are generated at predetermined angular positions of the measuring unit, these sets of data being supplied from the radiation receiver 3 to a computer 7 that calculates the attenuation coefficients of predetermined picture elements (pixels) from the generated data sets and visually reproduces them on a monitor. Accordingly, an image hereinafter referred to as a "tomogram" of the x-ray scanned section of the patient appears on the monitor 8.

Figure 2:
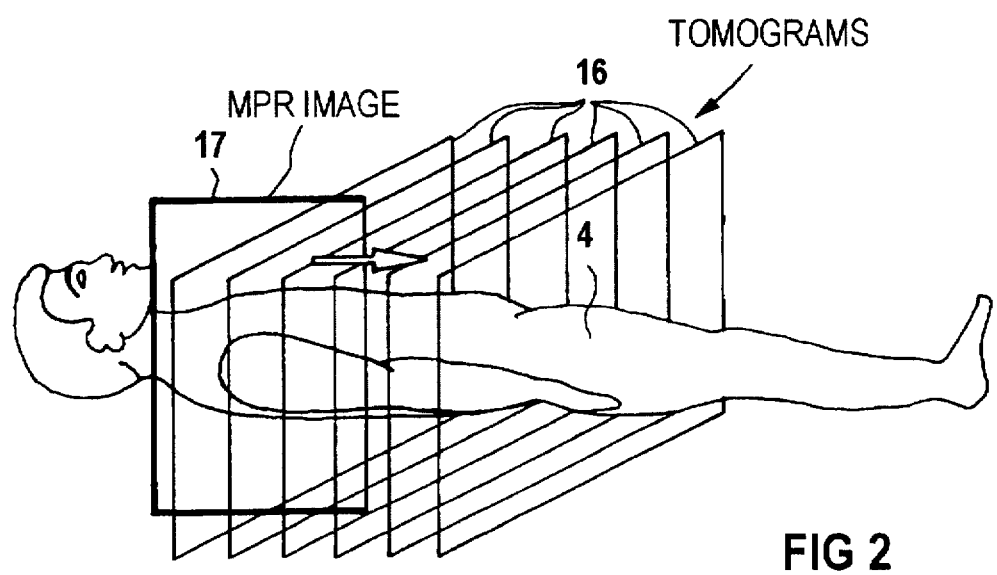
FIG. 2 shows sectional illustrations for explaining the inventive method.

A number of parallel tomograms 16 according to FIG. 2 can be generated by scanning a number of parallel slices of the patient 4. The tomograms 16 represent the volume elements (voxels) of the measures volume at the position of pixels in a special transaxial plane. An MPR sectional image 17 is to be displayed from the image data or voxel data of the tomograms 16. FIG. 2 refers to tomograms as the reconstructed image, but the reconstructed image can alternatively be a sub-volume image.

The position of the desired MPR sectional image 17 is defined before the beginning of the reconstruction (the calculation of the individual tomograms). When the sectional image 17 is a plane, the specification of one point of the plane as well as of the normal vector of the plane suffices. For more general orientations of the desired MPR sectional image 17, a correspondingly more extensive description is necessary.

The resolution with which the MPR image 17 is to be displayed is also specified (e.g. in pixel/cm).

The section line with the desired MPR sectional image 17 is directly calculated by one- or two-dimensional interpolation between the pixels of the tomogram. This is done for each reconstructed individual tomogram 16 of the image volume and is stored for later usage. For the special case wherein the MPR sectional image 17 is a plane image, the section line works out as a straight line. Dependent on the selected resolution of the MPR sectional images the new values are calculated by interpolation or by averaging of the preprocessed and stored values of the section lines. For an equal or higher resolution of the new image an interpolation is unproblematical. For lower resolution, that means the original section lines are lying closer together than required for the defined resolution of the MPR image, the average is calculated by weighted addition of the neighboring section lines in order to reduce noise and to use all available information for the reformatted image.

The degree of interpolation or weighting can be predetermined. The degree defines the number of section lines necessary for calculating an image line of the MPR sectional image 17. These section lines are intermediately stored in the reconstruction computer. Older section lines no longer required for the interpolation can be erased or dumped and so their memory area is again available for storage. Dependent on the degree of interpolation or weighting more or less computing time is necessary and therefore a slight lag in the output of the lines of the MPR sectional image 17 compared to the reconstructed sectional image may possibly have to be accepted.

Dependent on the orientation of the MPR sectional image 17, an additional interpolation within the section line possibly may be required in order to obtain values at the required pixel positions of an image. This interpolation can be processed together with the above-described interpolation of intermediate section lines, as one step of the in total two- or three-dimensional interpolation.

The inventive procedure can be summarized as follows.

First, the position of the desired MPR image is specified. This is accomplished by providing the pixel coordinates of the MPR image in the k, l, m directions, i.e. $x_i=(X_{ik}, X_{il}, X_{im})$ for i=1 ... N, where N is the total number of pixels in the MPR image. In the special case of a plane the position is defined by $(x-p)n=0$, where p is a point in the plane and n is the plane's normal vector, and x is usually evaluated at pixel coordinates $(x_{ik}, x_{il}, x_{im})$ which are equidistant in each direction.

The respective positions of the tomogram images are identified by their pixel positions $x_j=(x_{jk}, x_{jl}, x_{jm})$.

An interpolation and/or weighting function is specified which, in general, is a function h (x) of the three spatial coordinates $(X_k, X_l, X_m)$. For special cases a separable function $h(x)=h_1(x_k, x_l)h_3(x_m)$ or $h(x)=h_1(x_k)h_2(x_l)h_3(x_m)$ can be used. A scaling of the interpolation function suited to the specified resolution of the MPR image is implemented. The two- or three-dimensional interpolation can be carried out as a number of one-dimensional interpolations, also. The different realizations differ in compute time and accuracy of the calculation.

Figure 3:
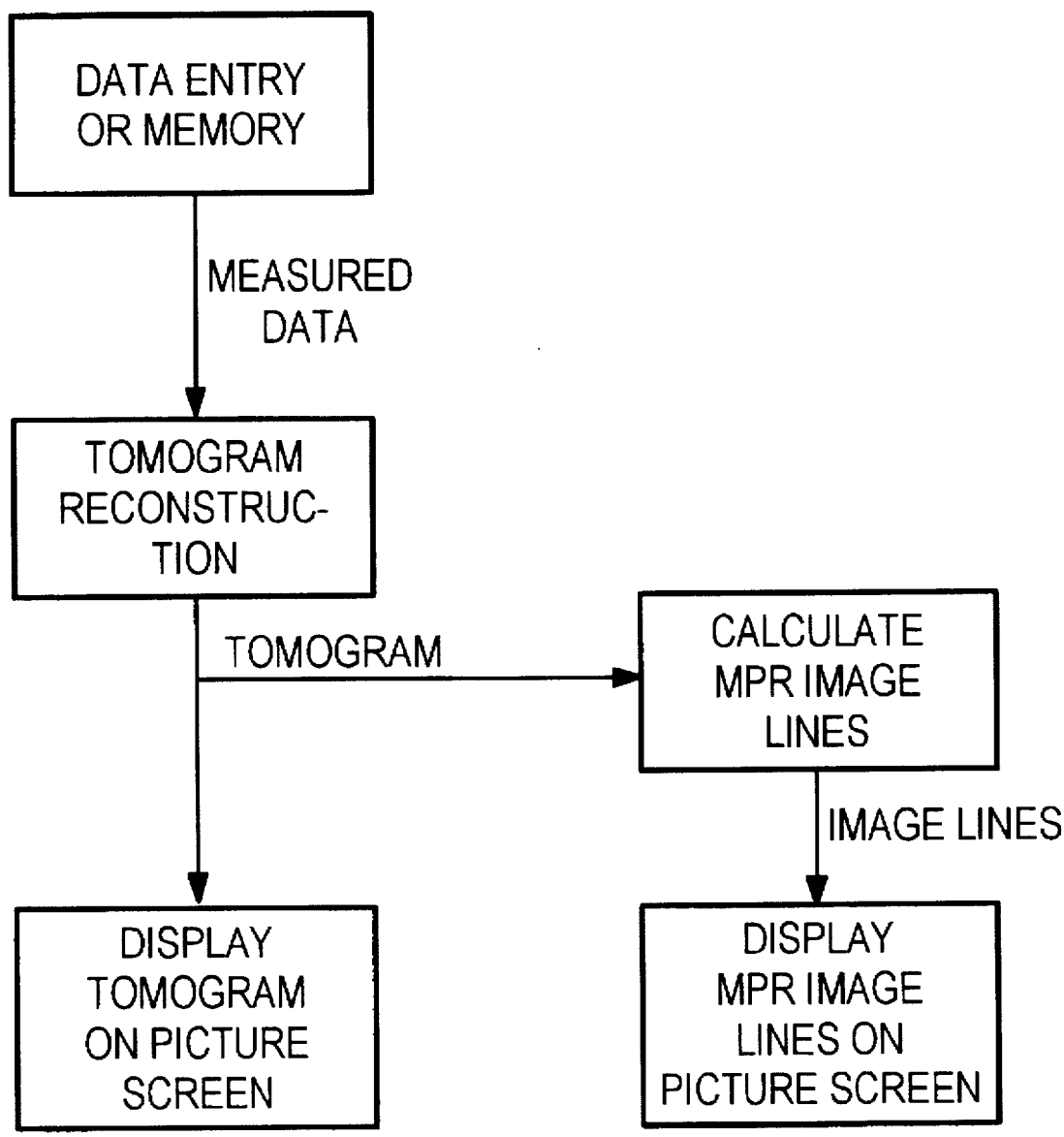
FIG. 3 is a flow chart for explaining the embedding of the calculation into the reconstruction of tomograms given the computed tomography of FIG. 1 in conformity with FIG. 2.

The image lines of the MPR sectional image 17 calculated in this way are immediately forwarded for display at the screen of the monitor 8. The method according to FIG. 3 can be employed for computed tomography. Further, it can also be applied to other imaging methods wherein three-dimensional image data are used to calculate two-dimensional tomograms or to calculate sub-volume image data, i.e., wherein any type of reconstructed image is calculated. Differing alignment or density of the tomograms or sub-volume image data describing the volume image do not constitute any limitation on the applicability of the method.

Advantages of the method are the fast presentation of the MPR image keeping pace (simultaneous) with the calculation of the image volume ("growing MPR"), and the reduction of the necessary memory in the reconstruction computer since only a few section lines need to be intermediately stored instead of the whole sequence of tomograms.

The generation of the image data for the tomograms 16 can be carried out by scanning a number of parallel slices of the patient 4, but can also be taken by a spiral scan.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating an image in an imaging system for a medical examination of a subject comprising the steps of:

obtaining measurements of an examination subject and acquiring a three-dimensional volume data set of said measurements;

using said three-dimensional volume data set, reconstructing a reconstructed image of said subject in a computer, said reconstructed image having image data associated therewith and having a reconstructed image orientation relative to said subject, and said reconstructed image being selected from the group consisting of a plurality of tomographic images of said subject and a sub-volume image of said subject; and substantially simultaneously with obtaining said measurements and reconstructing said reconstructed image, displaying an image data set, using said image data as a two-dimensional sectional image with an arbitrary orientation relative to said reconstructed image orientation, and on-line growing of said two-dimensional image on said display while acquiring said measurements and reconstructing said reconstructed image.

2. A method as claimed in claim 1 wherein the step of displaying said two-dimensional image comprises displaying said two-dimensional image as a two-dimensional sectional image, and comprising the additional step of defining a plane in said subject in which said two-dimensional sectional image is disposed by a point and a normal vector of said plane.

3. A method as claimed in claim 2 comprising the additional step of selecting a resolution of said two-dimensional image.

4. A method as claimed in claim 2 comprising the step of generating said two-dimensional image from said image data by interpolation of intermediate values between lines of said two-dimensional image.

5. A method as claimed in claim 4 wherein the step of interpolation comprises a two- or three-dimensional interpolation divided into one-dimensional interpolations.

6. A method as claimed in claim 1 comprising the additional step of defining any cross-sectional curved shape or surface in said subject and wherein the step of displaying said two-dimensional image comprises displaying said shape or surface as said two-dimensional image by a geometrical function or a listing of fixed points within said shape or surface.

7. A method as claimed in claim 1 wherein the step of reconstructing said reconstructed image of said subject comprises reconstructing a plurality of tomographic images of said subject, and wherein the step of displaying said image data set in the form of a two-dimensional image comprises directly calculating a section line for each of said plurality of tomographic images.

8. A method as claimed in claim 1 comprising the additional step of displaying said two-dimensional image immediately upon or parallel to the calculation thereof from said image data set.

9. A method as claimed in claim 1 wherein the step of acquiring said measurements comprises acquiring said measurements of said examination subject in a computed tomography apparatus.

* * * * *